May 11, 1965 A. M. SHAMMARELLO Plant Pat. 2,507
AZALEA PLANT
Filed Nov. 5, 1963
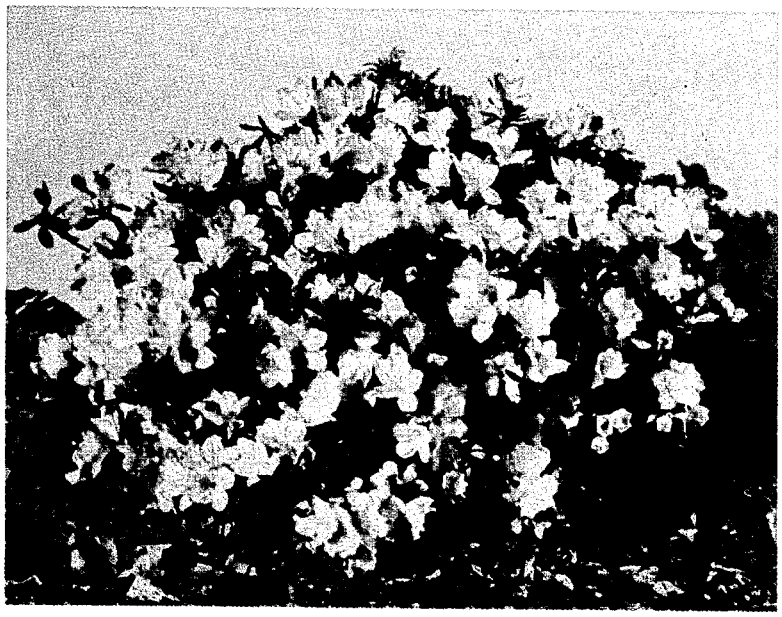

United States Patent Office

Plant Pat. 2,507
Patented May 11, 1965

2,507
AZALEA PLANT

Anthony M. Shammarello, 4590 Monticello Blvd., Cleveland, Ohio

Filed Nov. 5, 1963, Ser. No. 321,709
1 Claim. (Cl. Plt.—57)

The present invention relates to a new and distinct variety of azalea plant of the Kurume type, and is the result of a definite breeding program.

The principal object of this breeding program was to produce a new variety of azalea plant having greater hardiness than any similar dwarf evergreen azalea known to me in the northern part of Ohio, and having radiant red flowers larger than the Hino-Crimson parent, together with a plant with the Kurume character of growth. The foregoing object has been obtained in my new variety, which is characterized by a hardier plant, hardier flower buds than the Kurume parent, larger radiant red non-fading flowers when exposed to sun, and the retention of foliage throughout the winter, together with the bushy character of growth of the Kurume parent.

*Seed parent.*—An unnamed seedling derived from crossing Hino-Crimson × Poukhanense.

*Pollen parent.*—An unnamed seedling derived from crossing a red Kaempferi seedling × James Gable.

All parents were unpatented varieties.

My new variety has been found to retain its distinctive characteristics through successive asexual reproduction by means of cutting in the vicinity of South Euclid, Ohio.

The hardiness of the plant and flower buds of my new variety is indicated by the fact that they were not adversely affected by a temperature of −19° F. during the winter of 1962–1963 in the vicinity of South Euclid, Ohio.

The flowers of my new variety are almost twice the size of the Kurume parent.

The accompanying drawing, forming a part hereof, shows a typical plant of my new variety of azalea, the color of the latter being as nearly true as it is reasonably possible to make the same in a color illustration of this character.

The following is a detailed description of my new variety of azalea plant, color references being to Nickerson Color Fan as published by Munsell Color Company.

Type: Hardy-evergreen.
Parent: Seedling.
*Seed parent.*—An unnamed azalea (azalea Hino-Crimson × Poukhanense).
*Pollen parent.*—An unnamed azalea (azalea red Kaempferi seedling × James Gable).

*Plant*

Form of plant: Bush; compact.
Growing habit: Medium; low branched; from a cutting attaining height of about eighteen inches and a width of about three feet in ten years.
Blooming season: About May 10th.
Young shoots: Stems—color 7.5R 3/6 moderate reddish brown.
Maturet shoots: Stems—color 2.5GY 5/5 moderate yellow green.
Foliage:
*Color of young leaves.*—5GY 4/3 moderate olive green.
*Color of mature leaves.*—5GY 3/2 grayish olive green.
*Color of hair on leaf.*—None.
*Arrangement of leaves.*—In a spiral.
*Form of leaves.*—Elliptical.
*Size of leaves*—1¼" to 1½" long.
*Size of leaves.*—½" to ⅜" wide.

*Flower*

Type: Single.
Borne: Usually three in a cluster.
Quantity: Abundant.
Form: Five petals, margins of lobes slightly frilled.
Size: Petal spread 1½" to 1¾" wide.
Blotch: None.
Color: 2.5R 4/10 moderate red.

*Reproductive Organs*

Stamens: Five to six; color—red.
Pistil:
*Color.*—Strong purplish red 10RP 4/12.
*Length.*—About 1¼ inches long; about ⅜ inch longer than stamens.

I claim:

A new and distinct variety of azalea plant of the hardy evergreen type, substantially as herein shown and described, characterized particularly as to novelty by the radiant red color of its flowers, by the absence of fading of the flowers when exposed to the sun, by the hardiness of the plant and buds at low temperatures greater than the parent Hino-Crimson, by flowers larger than the parent plant Hno-Crimson, and retaining the good qualities of the plant character of Hino-Crimson.

No references cited.

ABRAHAM G. STONE, *Primary Examiner.*